United States Patent [19]
Swallow

[11] Patent Number: 6,093,022
[45] Date of Patent: Jul. 25, 2000

[54] DENTAL DAM WITH INTEGRAL CLAMP

[76] Inventor: Stephen T. Swallow, 131 River Rd., West Newbury, Mass. 01985

[21] Appl. No.: 09/189,275

[22] Filed: Nov. 10, 1998

[51] Int. Cl.$^7$ ..................................................... A61C 5/14
[52] U.S. Cl. ........................................... 433/136; 433/139
[58] Field of Search ................................... 433/136, 137, 433/138, 139

[56] References Cited

U.S. PATENT DOCUMENTS

| | | | |
|---|---|---|---|
| 484,046 | 10/1892 | Pitman | 433/136 |
| 1,550,425 | 8/1925 | Burlew | 433/136 |
| 1,604,136 | 10/1926 | Stoloff | 433/137 |
| 1,774,285 | 8/1930 | Middaugh | 433/137 |
| 2,092,549 | 9/1937 | Craigo | 433/136 |
| 2,106,252 | 1/1938 | Luongo | 433/40 |
| 2,835,628 | 5/1958 | Saffir | 433/39 |
| 2,846,927 | 8/1958 | Masci et al. | 132/321 |
| 3,406,452 | 10/1968 | McConville | 433/137 |
| 3,478,432 | 11/1969 | Gross | 433/137 |
| 3,662,466 | 5/1972 | McConville | 433/137 |
| 3,781,994 | 1/1974 | Hesselgren | 433/137 |
| 3,903,232 | 9/1975 | Wood et al. | 264/157 |
| 4,240,789 | 12/1980 | Rosenthaler | 433/136 |
| 4,259,067 | 3/1981 | Nelson | 433/93 |
| 4,344,758 | 8/1982 | Wielhouwer et al. | 433/137 |
| 4,773,857 | 9/1988 | Herrin | 433/138 |
| 5,340,313 | 8/1994 | Hussin | 433/136 |
| 5,462,067 | 10/1995 | Shapiro | 128/861 |

FOREIGN PATENT DOCUMENTS 691 434  6/1937  Germany .

*Primary Examiner*—John J. Wilson
*Attorney, Agent, or Firm*—Cantor Colburn LLP

[57] ABSTRACT

An improved dental dam includes a sheet of moisture impervious material integrally attached to at least one and preferably at least two thickened areas. The thickened areas may be of the same material or a different material. Preferably latex is the material for both the sheet material and the thickened area which constitutes a clamp. The clamp, having surfaces oriented to closely match the surface profile of a tooth are treated with an adhesive material which will bond with the tooth to be clamped.

15 Claims, 1 Drawing Sheet

DENTAL DAM WITH INTEGRAL CLAMP

BACKGROUND OF THE INVENTION

1. Field of the Invention

The invention relates to the field of dentistry. More particularly, the invention relates to an improved dental dam wherein the clamp is integrally formed with the sheet material and is adhesively securable to the tooth to be clamped.

2. Prior Art

The field of dentistry has been using different means of isolating teeth from saliva, other teeth, tongue, etc. for 50 years or more. Such isolation is advantageous because it helps to avoid the patient's saliva contaminating the work area and restoring material and additionally prevents debris from tooth preparation or the like from being distributed around the mouth of the patient.

Traditionally, rubber dams are mounted in the patients mouth with a metal clamp. The metal clamp is installed first on a suitable anchor tooth and then the rubber dam is stretched around the metal clamp and allowed to slide thereunder whereupon the dam is held securely in place.

Although metal clamps are effective for their intended purpose they can cause discomfort to the patient without anesthesia being administered and can be difficult to work with. The clamps are small but are large enough to obstruct a patient's airway should they be dropped therein The placement of metal clamps is also time consuming which is undesirable to both patient and doctor. Time is consumed by the need to tie a "safety line" of floss to each clamp used for withdrawal from the patient's airway if the clamp falls therein.

Moreover time is consumed by the usual need to try several different sizes before a suitable size is determined. Another drawback to conventional metal clamps is that the height of contour of a tooth cannot always be reached which means that a stable placement of the metal clamp is impossible. Trauma to soft tissues is yet another problem associated with metal clamps. The metal clamp can press into the soft gingival tissue and do temporary or even permanent damage thereto. Finally, metal clamps tend to restrict access to the clamped tooth and therefore hinder the dental procedure being undertaken. Because of this, dams are not always employed when indicated. The art, then, is in need of an improvement in this technology.

SUMMARY OF THE INVENTION

The above-identified drawbacks of the prior art are overcome or alleviated by the integral dental dam and clamp of the invention.

The invention comprises a sheet of rubber dam material preferably latex (although other materials are substitutable), which in large part is conventional, being provided with an integral clamp. The clamp is preferably comprised of rubber of the same type as the dam and is simultaneously molded into the rubber dam material. It should be understood, however, that other materials may also be used and the clamp could be attached to the sheet dam subsequently to production of the dam material. The clamp comprises two projections from the dam material that are specifically shaped to proximately follow the buccal and lingual aspects of a tooth to be clamped. The inner surface of these projections are treated with an adhesive that is selectively bondable to a tooth. The rubber clamp of the invention completely replaces the metal clamp of the prior art.

By avoiding the use of a metal clamp, many of the drawbacks connected with the use of dental dams are alleviated for example, no safety line (dental floss) is required prior to the dam and clamp of the invention being inserted in the mouth of the patient; the invention is far less uncomfortable to the patient; the formed rubber clamp structure of the invention reduces the time required to install the rubber dam in the mouth of the patient as well as substantially avoiding pain and potential damage to soft tissues associated with such an installation when it is not otherwise advantageous to administer anaesthesia for the procedure; the invention is easier to use and does not obstruct access to the clamped tooth; stable placement is virtually assured.

BRIEF DESCRIPTION OF THE DRAWINGS

Referring now to the drawings wherein like elements are numbered alike in the several FIGURES.

DETAILED DESCRIPTION OF THE INVENTION

Figure 1:
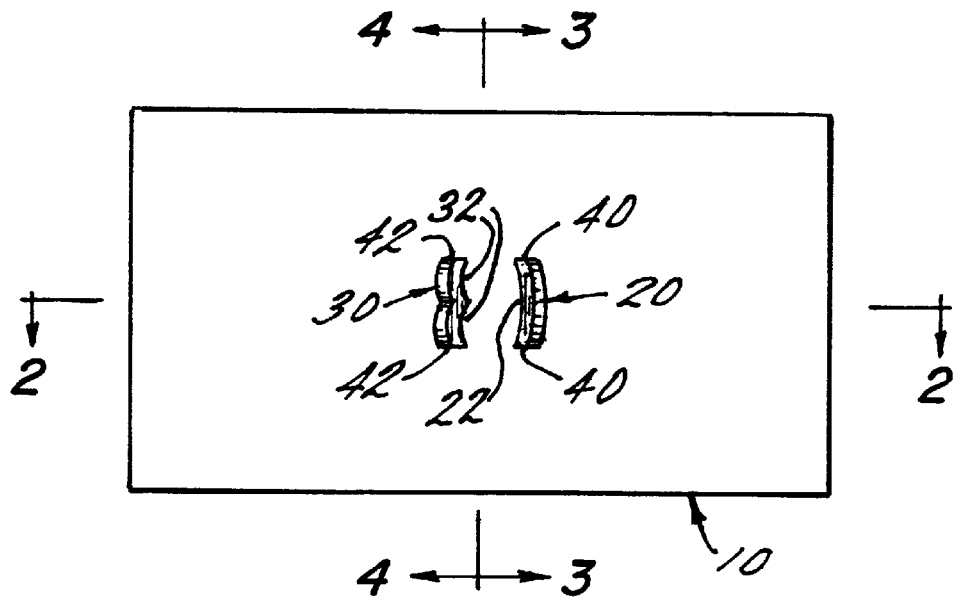
FIG. 1 is a bottom plan view of the dental dam having an integral clamp of the invention.

Referring to FIG. 1, a bottom plan view of a dental dam with an integral rubber clamp is illustrated. The sheet 10, which is generally a conventional member, is provided, in the invention, with projections 20 and 30. In one embodiment of the invention, projection 20 is shaped to generally mate with the lingual aspect of a molar in a patient's mouth (may also be designed to mate with other teeth). In general, most people have a convexity to the lingual aspects of their molars; thus the invention provides a concavity in the lingual projection 20 to mate with the convexity of the tooth. The specific curvature is not critical as it is intended that the invention herein be employed for the majority of people. Moreover, the clamp of the invention is pliable and will form to the tooth. The invention will function as desired providing the projection generally mates with the teeth.

The concavity of projection 20 is defined by surface 22. Surface 22 will carry an adhesive described more fully hereunder. Projection 20 is preferably about 1.7 to about 1.8 millimeters high or deep relative to the reference height defined by the sheet 10. It is to be understood that the term "high" is used only relatively and it should be recalled that in at least one embodiment of the invention, the projections of the invention are intended to extend downwardly from sheet 10. Preferably projection 20 is 1.0–1.5 millimeters wide and is approximately 9 millimeters long for a molar tooth.

The second projection, 30, is oriented on sheet 10 as illustrated to be complimentary to the buccal aspect of the molar to be clamped. As can easily be ascertained from the illustration, projection 30 includes a double concavity in the surface 32 which faces the surface 22 of projection 20. Surface 32 is shaped to generally mate with the buccal aspect of the majority of people and this carries a general shape as does projection 20 as opposed to an overly specific surface. Surface 32 is also treated with an adhesive material to allow the surface to adhere to the molar to be clamped. In the embodiment illustrated, projection 30 is about 9 millimeters long and 1.0–1.5 millimeters wide, similar to projection 26. Projections 20 and 30 are preferably about 5½ millimeters apart at the centerline (along section line 2—2) and about 3½ millimeters apart at the ends 40 and 42, respectively, thereof. Other embodiments of the invention may have different sizes as desired.

A hole is punched between the two projections to accept through passage of a tooth to be clamped. Other holes may be punched for additional teeth in the arch as desired and as is conventional. Holes may be prepunched or punched for use.

Figure 2:
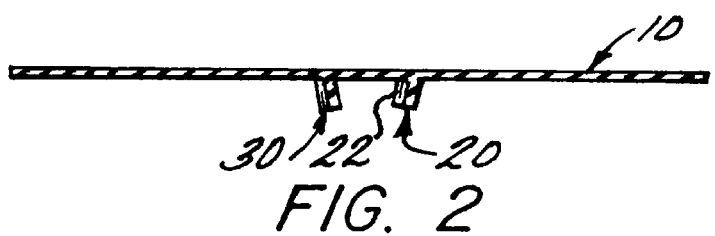
FIG. 2 is a cross section view of the dental dam of the invention taken along section line 2—2 in FIG. 1.
Figure 3:
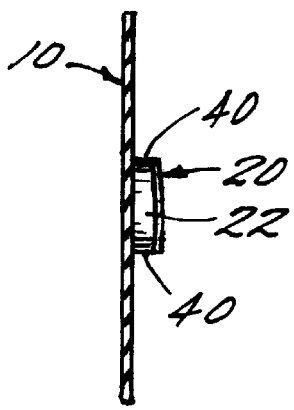
FIG. 3 is a cross section view of the dental dam of the invention taken along section line 3—3 in FIG. 1.
Figure 4:
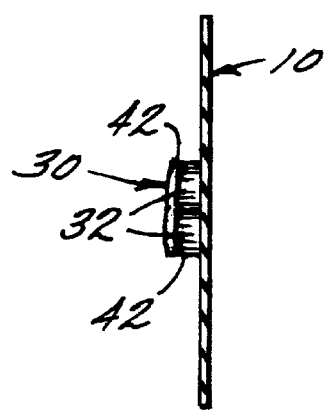
FIG. 4 is a cross section view of the dental dam of the invention taken along section line 4—4 in FIG. 1.

Each of the projections is angled toward each other (visible only in FIG. 2) by about 15 degrees. The angularity helps to ensure a reliable contact with the molar being clamped. This is because typically molars are larger on top and become more narrow as they meet the gingiva. The clamp could also extend upwardly instead of downwardly with corresponding change to the angularity, i.e. the clamp projections angle away from each other.

As one of skill in the art may recognize, the stretching and rebound of the sheet 10 provides some retention for the sheet on the tooth but this is insufficient. Thus, the adhesive is placed upon surfaces 22 and 32 as hereinbefore stated. The preferred adhesive is a selectively activated type so that the clamp may easily be properly positioned around a tooth before the adhesive is activated. A non-selective adhesive could be substituted but would make placement of the dam and clamp more difficult. Preferably, the adhesive material is double sided (whether with a backing material or without between the adhesives—having no backing is preferred) with one side being adhereable to a dry surface (i.e. to the clamp) and the other side being adhereable to a wet surface (i.e. the tooth).

The invention is put into service by assessing the mouth of the patient for a suitable tooth to be clamped. The hole for the clamped tooth is preferably pre-punched and holes are then punched conventionally for any others requiring isolation. Once holes are properly punched, a protective covering on the adhesive having been previously applied, is removed from each projection and the rubber dam inserted by stretching the sheet 10 to urge the projection down over the tooth and into contact with the gingival margins on the buccal and lingual aspects of the tooth. With the clamp in this position the adhesive is activated preferably by a spray of water. The rubber to the mesial and distal is then flossed through the interproximal contacts of the isolated teeth and the dental procedure to be performed can be commenced.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. An improved dental dam comprising:
   a sheet;
   at least one projection from one major surface of said sheet, said at least one noncircular projection being preformed to generally follow one of a lingual and a buccal surface of a tooth and adapted to mate with said surface of said tooth; and
   at least one adhesive provided on one surface of said at least one projection.

2. An improved dental dam as claimed in claim 1 includes two projections in spaced apart relation and wherein one projection is adapted to mate with a tooth on a lingual side of said tooth and the other projection is adapted to mate with said tooth on a buccal side of said tooth.

3. An improved dental dam as claimed in claim 2 wherein said adhesive is placed upon one side of each projection, said one side of each projection being sides facing and spaced from each other.

4. An improved dental dam as claimed in claim 2 wherein said two projections are integrally formed with said sheet.

5. An improved dental dam as claimed in claim 2 wherein said projections extend outwardly from said major surface of said sheet in the range of about 1.7 to 1.8 millimeters.

6. An improved dental darn as claimed in claim 2 wherein said projections are generally arcuate and are spaced apart centrally by about 5 to about 6 millimeters and at ends thereof by about 3 to about 4 millimeters.

7. An improved dental dam as claimed in claim 6 wherein said projections are about 9 millimeters long.

8. An improved dental dam as claimed in claim 1 wherein said adhesive is selectively activated.

9. An improved dental dam as claimed in claim 1 wherein said adhesive is water activated.

10. An improved dental dam as claimed in claim 1 wherein said at least one projection is integrally formed with said sheet.

11. An improved dental dam comprising:
    a sheet;
    a first projection and a second projection attached to said sheet in spaced apart relation and wherein one of said first projection and said second projection is adapted to mate with a tooth on a lingual side of said tooth and the other of said first projection and said second projection is adapted to mate with said tooth on a buccal side of said tooth, and wherein said first projection and said second projection are of different geometric shapes selected to coincide with the lingual or the buccal side of a tooth; and
    at least one adhesive provided on one side surface of said at least one projection.

12. A dental dam comprising:
    a sheet;
    a first noncircular projection mounted to one major surface of said sheet;
    a second noncircular projection mounted to the same said surface of said sheet, said first and second projections being preformed to generally follow one of a lingual and a buccal surface of a tooth and adapted to mate with said surface of said tooth and being spaced apart and bordering an opening in said sheet; and
    an adhesive on each of said projections on surfaces thereof facing each other.

13. A method for installing a dental dam in a patient's mouth comprising:
    identifying a tooth around which said dam is to be clamped;
    placing a sheet portion in said patient's mouth by positioning said sheet portion over said tooth, said sheet portion having at least one noncircular projection being preformed to generally follow at least one of a lingual and a buccal surface of a tooth, said projection extending toward a gingiva of said patient's mouth;

clamping said dental dam to said tooth; and activating at least one inactivated adhesive on said projection to adhere said dental dam to said tooth.

14. A method as claimed in claim 13 wherein said clamping includes stretching said sheet portion of said dental dam and an opening therein adjacent at least one projection protruding from said sheet portion over said tooth to be clamped; and manipulating said sheet portion in said patient's mouth such that a hole in said sheet portion receives said tooth therethrough and at least one projection on said sheet portion engages at least one side of said tooth.

15. A method as claimed in claim 13 wherein said installing includes punching additional openings in said sheet portion to receive at least one other tooth in said patient's mouth; and flossing mesial and distal portions of material from said sheet portion into openings and through interproximal contacts of teeth in said patient's mouth.

* * * * *